United States Patent [19]
Tang et al.

[11] Patent Number: 5,811,605
[45] Date of Patent: Sep. 22, 1998

[54] PREPARATION OF 1,2,3,3-TETRACHLOROPROPENE

[75] Inventors: Robert H. Tang, Murrysville; G. V. Bindu Madhavan; Yingchao Zhang, both of Monroeville, all of Pa.

[73] Assignee: PPG Industries, Inc., Pittsburgh, Pa.

[21] Appl. No.: 802,704

[22] Filed: Feb. 19, 1997

[51] Int. Cl.$^6$ .................................................. C07C 21/00
[52] U.S. Cl. .......................................... 570/226; 570/228
[58] Field of Search ...................... 570/228, 226

[56] References Cited

U.S. PATENT DOCUMENTS

| | | | |
|---|---|---|---|
| 3,823,195 | 7/1974 | Smith | 260/654 R |
| 3,859,441 | 1/1975 | Moon | 422/277 |
| 3,878,188 | 4/1975 | L'Eplattenier et al. | 260/146 R |
| 3,926,758 | 12/1975 | Smith | 204/163 |
| 4,225,719 | 9/1980 | Frishberg | 548/194 |
| 4,239,760 | 12/1980 | Sasse et al. | 424/249 |
| 4,239,901 | 12/1980 | Rainer | 560/34 |
| 4,722,905 | 2/1988 | Honeybourne et al. | 436/151 |
| 4,751,309 | 6/1988 | Daltrozzo et al. | 546/176 |
| 4,876,347 | 10/1989 | Daltrozzo et al. | 546/176 |
| 4,952,694 | 8/1990 | Brackeen et al. | 546/15 |
| 4,960,890 | 10/1990 | Daltrozzo et oa. | 544/353 |
| 5,006,657 | 4/1991 | Brackeen et al. | 546/18 |
| 5,206,367 | 4/1993 | Urban | 546/15 |

FOREIGN PATENT DOCUMENTS 261689  3/1912  Netherlands .

OTHER PUBLICATIONS

Lovelace Aliphatic Fluorine Compounds 1958 pp. 101,102.

Abstracts of Papers on Organic Chemistry, Journal of the Chemical Society, London, Gurney & Jackson, (1913), p. i.1037.

H. J. Prins and F. J. W. Engelhard, "Syntheses of Polychloro Compounds. II. The catalytic action of aluminum chloride in the reaction between chloroform and dichloroethylene", pp. 307–312.

J. W. Cornforth et al, "A Synthesis of Acylamidomalondialdehydes", Journal of the Chemical Society, (1949), pp. 1549–1553.

*Primary Examiner*—Alan Siegel
*Attorney, Agent, or Firm*—George D. Morris

[57] ABSTRACT

The dehydrochlorination of 1,1,2,3,3-pentachloropropane to produce 1,2,3,3-tetrachloropropene is conducted using aqueous alkali metal hydroxide in the substantial absence of added ethanol.

The 1,2,3,3-tetrachloropropene is recovered from the reaction mixture in the substantial absence of added ether. The preferred methods of recovery are steam distillation and flash distillation.

14 Claims, No Drawings

PREPARATION OF 1,2,3,3-TETRACHLOROPROPENE 1,2,3,3-Tetrachloropropene [CAS 20589-85-9] (hereinafter "TCP") is a known compound having many uses, especially as an intermediate in the manufacture of many agricultural and pharmaceutical products. See, for example, J. W. Cornforth et al, *Journal of the Chemical Society*, 1949, pages 1549–1553, and U.S. Pat. Nos. 4,952,694; 5,066,657; and 5,206,367. TCP is also useful as an intermediate in the preparation of 1,1,2,3,3-pentafluoropropane [CAS 24270-66-4] which is an environmentally friendly hydrofluorocarbon cleaning agent.

A known preparation of TCP is the dehydrochlorination of 1,1,2,3,3-pentachloropropane [CAS 15104-61-7] using a solution of potassium hydroxide in ethanol (viz., an ethanolic solution of potassium ethoxide), followed by extraction using water and ether. See J. W. Cornforth et al, *Journal of the Chemical Society*, 1949, pages 1549–1553.

A problem arising from using the known method is that of dealing with the ethanol which must be removed at some point in the process. Ethanol is both very volatile and water soluble in all proportions. It is therefore very difficult to use and dispose of ethanol without harm to the environment.

It has now been found that TCP may be prepared while using little or no ethanol in the dehydrochlorination process.

Accordingly, in the method wherein 1,2,3,3-tetrachloropropene is produced by the dehydrochlorination of 1,1,2,3,3-pentachloropropane, one embodiment of the invention is the improvement wherein the dehydrochlorination is conducted in an emulsion reaction mixture using aqueous alkali metal hydroxide in the substantial absence of added ethanol.

The phrase "in the substantial absence of added ethanol" means that no ethanol is added to perform a chemical or solvating function. It is noted, however, that small amounts of ethanol which may find their way into the system as impurities or the like, may be tolerated.

The 1,2,3,3-tetrachloropropene which is obtained by the above dehydrochlorination process may be cis-1,2,3,3-tetrachoropropene [CAS 34495-85-7], trans-1,2,3,3-tetrachloropropene [CAS 34495-84-6], mixture of both isomers. Usually the 1,2,3,3-tetrachloropropene which is obtained is a mixture of both isomers.

Any alkali metal hydroxide or mixtures of alkali metal hydroxides can be used. Usually the alkali metal hydroxide is lithium hydroxide, sodium hydroxide, potassium hydroxide, rubidium hydroxide, or a mixture of two or more thereof. Often the alkali metal hydroxide is lithium hydroxide, sodium hydroxide, potassium hydroxide, or a mixture of two or more thereof. Frequently the alkali metal hydroxide is sodium hydroxide, potassium hydroxide, or a mixture thereof. Sodium hydroxide is preferred.

The amount of alkali metal hydroxide used can vary widely. Usually at least a stoichiometric amount is employed. Often an excess of alkali metal hydroxide is used. The maximum amount is not governed by theory, but by practical considerations such as cost of materials and cost of disposals. In most instances the molar ratio of alkali metal hydroxide to 1,1,2,3,3-pentachloropropane is in the range of from 1:1 to 1.5:1.

The amount of water used can likewise vary considerably. Generally at least enough water is present to solubilize the alkali metal hydroxide. The maximum amount is not governed by theory, but by practical considerations such as cost of operations.

The temperature at which the dehydrochlorination is conducted may vary widely. Usually the temperature is in the range of from 5° C. to 95° C. Often the temperature is in the range of from 20° C. to 90° C. From 40° C. to 85° C. is preferred.

Once the dehydrochlorination reaction has been concluded, the TCP is usually recovered from the reaction mixture and purified. The known method is that disclosed by Cornforth et al, supra, were following dehydrochlorination in an ethanolic solution of potassium hydroxide, water was added, and the ether was added to isolate the TCP.

A problem arising from using the known method is that of dealing with the ether which must be recovered at some point in the process. Ether is both very volatile and very flammable. It is therefore very difficult to use and dispose of ether safely and without harm to the environment.

It has now been found that TCP may be recovered from a dehydrochlorination reaction mixture while using little or no ether. In this particular case an emulsion is formed during the reaction which facilitates the dehydrochlorination process. Neither organic solvent nor phase transfer catalyst is required and the emulsion may later be broken by distillation for easy separation of the product.

Accordingly, in the method wherein 1,2,3,3-tetrachloropropene is recovered from a reaction mixture produced by the dehydrochlorination of 1,1,2,3,3-pentachloropropane, another embodiment of the invention is the improvement wherein:

(a) the reaction mixture from which the 1,2,3,3-tetrachloropropene is recovered is an emulsion reaction mixture, and (b) the recovery is conducted in the substantial absence of added ether.

The phrase "in the substantial absence of added ether" means that no ether is added to perform a chemical or solvating function. It is noted, however, that small amounts of ether which may find their way into the system as impurities or the like, may be tolerated.

The preferred method of recovery of TCP is distillation of the reaction mixture.

Accordingly, in the method wherein 1,2,3,3-tetrachloropropene is recovered from a reaction mixture produced by the dehydrochlorination of 1,1,2,3,3-pentachloropropane, yet another embodiment of the invention is the improvement wherein:

(a) the reaction mixture from which the 1,2,3,3-tetrachloropropene is recovered is an emulsion reaction mixture; and (b) the recovery is conducted by distillation.

The preferred methods of distillation are steam distillation and flash distillation.

Other than in the operating examples, or where otherwise indicated, all numbers expressing quantities of ingredients or reaction conditions used herein are to be understood as modified in all instances by the term "about".

The invention is further described in conjunction with the following examples which are to be considered illustrative rather than limiting, and in which all parts are parts by weight and all percentages are percentages by weight unless otherwise specified.

EXAMPLE 1

A 2-liter, four-necked flask fitted with a reflux condenser, a mechanical stirrer, and an electric heating mantle was charged with 701 grams of 1,1,2,3,3-pentachloropropane. Next, 705 grams of a 25% aqueous sodium hydroxide solution were added. The reaction mixture was allowed to warm to 45° C. and stirred at that temperature for 4 hours until 1,1,2,3,3-pentachloropropane was not detectable by gas chromatography. The resulting mixture was a black liquid emulsion. Six hundred grams of distilled water were added to the emulsion and the resulting reaction mixture was placed in a Buchi Rotavapor® distillation apparatus. An azeotropic mixture was removed at 60° C. and phase separated. The bottom organic layer was a colorless liquid which weighed 505 grams and had a boiling point of 164° C. The water content of the product was 0.072%. The product was identified as 1,2,3,3-tetrachloropropene of 95% purity. The yield was 82.3 percent.

EXAMPLE 2

Into a 12-liter four-necked flask equipped with condenser, addition funnel, mechanical stirrer, heating mantle, and thermometer connected to a Therm-O-Watch® temperature control unit were added 53.6 grams of anhydrous aluminum chloride catalyst and 6.23 kilograms of chloroform. The pale yellow cloudy mixture was warmed to 40° C. to 45° C. and 3.9 kilograms of a 4:1 mixture of cis-1,2-dichloroethene and trans-1,2-dichloroethene were added in portions to raise and keep the temperature not exceeding 70° C. with a gentle reflux in the condenser. This took about 4 hours and no reflux was observed at the end of addition. The reaction mixture was cooled to 19° C. and 200 milliliters of water were added in portions. The water addition resulted in a small temperature rise to 28° C. The reaction mixture was distilled under vacuum (13.5 kilopascals, absolute pressure at the pot) until a mixture of chloroform and 1,2-dichloroethene weighing 2.24 kilograms and 94 grams of water were collected as distillate. The pot temperature during distillation was from 26° C. to 51° C. while the overhead temperature was about 30° C. To the rest of the batch in the reactor at an initial temperature of about 50° C., 3.5 kilograms of a 25% by weight aqueous sodium hydroxide solution were added in portions. The addition raised the temperature to 80° C. The reaction mixture was cooled to 45° C. and a further 3.5 kilograms of 25% by weight aqueous sodium hydroxide solution were added. The reaction mixture was stirred overnight without any external heating and then distilled under vacuum (6.7 to 16.9 kilopascals, absolute pressure at the pot). The pot temperature during distillation was from 30° C. to 60° C. while the overhead temperature was from 22° C. to 50° C. The product obtained was a colorless liquid weighing 5.2 kilograms. The product was identified as a mixture of cis-1,2,3,3-tetrachloropropene and trans-1,2,3,3-tetrachloropropene which mixture had a gas chromatographic assay of 95%. The yield based on 1,2-dichloroethene charged was 72%.

Although the present invention has been described with reference to specific details of certain embodiments thereof, it is not intended that such details should be regarded as limitations upon the scope of the invention except insofar as they are included in the accompanying claims.

We claim:

1. In the method wherein 1,2,3,3-tetrachloropropene is produced by the dehydrochlorination of 1,1,2,3,3-pentachloropropane, the improvement wherein the dehydrochlorination is conducted in an emulsion reaction mixture using aqueous alkali metal hydroxide in the substantial absence of added ethanol.

2. The method of claim 1 wherein said alkali metal hydroxide is sodium hydroxide, potassium hydroxide, or a mixture thereof.

3. The method of claim 1 wherein said alkali metal hydroxide is potassium hydroxide.

4. The method of claim 1 wherein said alkali metal hydroxide is sodium hydroxide.

5. The method of claim 1 wherein the temperature at which the dehydrochlorination is conducted is in the range of from 5° C. to 95° C.

6. The method of claim 1 wherein the temperature at which the dehydrochlorination is conducted is in the range of from 20° C. to 90° C.

7. The method of claim 1 wherein the temperature at which the dehydrochlorination is conducted is in the range of from 40° C. to 85° C.

8. In the method wherein 1,2,3,3-tetrachloropropene is recovered from a reaction mixture produced by the dehydrochlorination of 1,1,2,3,3-pentachloropropane, the improvement wherein:

(a) the reaction mixture from which the 1,2,3,3-tetrachloropropene is recovered is an emulsion reaction mixture; and (b) the recovery is conducted in the substantial absence of added ether.

9. In the method wherein 1,2,3,3-tetrachloropropene is recovered from a reaction mixture produced by the dehydrochlorination of 1,1,2,3,3-pentachloropropane, the improvement wherein:

(a) the reaction mixture from which the 1,2,3,3-tetrachloropropene is recovered is an emulsion reaction mixture; and (b) the recovery is conducted by distillation.

10. The method of claim 9 wherein said distillation is steam distillation.

11. The method of claim 9 wherein said distillation is flash distillation.

12. In the method wherein 1,2,3,3-tetrachloropropene is produced by the dehydrochlorination of 1,1,2,3,3-pentachloropropane and the 1,2,3,3-tetrachloropropene so produced is recovered from the reaction mixture, the improvement wherein:

(a) the dehydrochlorination is conducted using aqueous alkali metal hydroxide in the substantial absence of added ethanol;

(b) an emulsion reaction mixture is formed during the dehydrochlorination reaction;

(c) the 1,2,3,3-tetrachloropropene is recovered from the emulsion reaction mixture; and (d) the recovery of 1,2,3,3,-tetrachloropropene from the emulsion reaction mixture is conducted in the substantial absence of added ether.

13. The method of claim 12 wherein:

(a) said alkali metal hydroxide is sodium hydroxide;

(b) the temperature at which the dehydrochlorination is conducted is in the range of from 5° C. to 95° C.; and (c) the recovery is conducted by distillation.

14. The method of claim 13 wherein the distillation is steam distillation or flash distillation.

* * * * *